(12) United States Patent
Tachibana et al.

(10) Patent No.: US 7,977,513 B2
(45) Date of Patent: Jul. 12, 2011

(54) METHOD AND APPARATUS FOR PRODUCING MONO-LOWER-ALKYLMONO-ALKANOLAMINE

(75) Inventors: Shinya Tachibana, Hiroshima (JP); Ryuji Yoshiyama, Nagasaki (JP); Tsuyoshi Oishi, Hiroshima (JP); Mikiya Sakurai, Hiroshima (JP); Kazuo Ishida, Kanagawa (JP); Tatsuya Tsujiuchi, Hiroshima (JP); Hidehisa Mita, Tokyo (JP); Ryosuke Araki, Tokyo (JP); Kenji Saito, Tokyo (JP)

(73) Assignees: Mitsubishi Heavy Industries, Ltd., Tokyo (JP); Nippon Nyukazai Co., Ltd., Tokyo (JP)

( * ) Notice: Subject to any disclaimer, the term of this patent is extended or adjusted under 35 U.S.C. 154(b) by 155 days.

(21) Appl. No.: 12/438,025

(22) PCT Filed: Aug. 6, 2007

(86) PCT No.: PCT/JP2007/065354
§ 371 (c)(1), (2), (4) Date: Feb. 19, 2009

(87) PCT Pub. No.: WO2008/068927
PCT Pub. Date: Jun. 12, 2008

(65) Prior Publication Data
US 2010/0249463 A1  Sep. 30, 2010

(30) Foreign Application Priority Data

Dec. 7, 2006  (JP) .................................. 2006-330544

(51) Int. Cl.
*C07C 213/00* (2006.01)
*C07C 213/04* (2006.01)
(52) U.S. Cl. ....................................... 564/477; 564/475

(58) Field of Classification Search ................... 564/477
See application file for complete search history.

(56) References Cited

U.S. PATENT DOCUMENTS

| 4,119,640 A | 10/1978 | Hodakowski et al. |
| 4,119,670 A | 10/1978 | Tsuchiya |
| 6,846,959 B2 * | 1/2005 | Garg et al. ................... 564/475 |

FOREIGN PATENT DOCUMENTS

| JP | 59-13751 A | 1/1984 |
| JP | 7-33718 A | 2/1995 |
| JP | 7-48327 A | 2/1995 |
| JP | 8-113602 A | 5/1996 |
| JP | 8-333310 A | 12/1996 |
| JP | 2000-204065 A | 7/2000 |
| JP | 2004-275933 A | 10/2004 |
| JP | 2007-217344 A | 8/2007 |

OTHER PUBLICATIONS

International Search Report of PCT/JP2007/065354, date of mailing Sep. 11, 2007.
Oda, Ryohei et al.; Surface Active Agent, 1965, pp. 262-263.

* cited by examiner

*Primary Examiner* — Brian J Davis
(74) *Attorney, Agent, or Firm* — Westerman, Hattori, Daniels & Adrian, LLP

(57) ABSTRACT

An amine producing apparatus includes a reactor that reacts a mono-lower-alkylamine and an alkylene oxide, an unreacted-raw-material-recovery distillation column that separates unreacted raw materials by distillation from a product including unreacted raw materials obtained in the reactor, a non-aqueous distillation column that removes water and a light component by a distillation method from a reactive product from which unreacted raw material have been separated, and a purification and distillation column that separates by distillation a desired reactive product (mono-lower-alkylmonoalkanolamine) and residue (mono-lower-alkyldialkanolamine which is a dimer) from a reactive product from which the water and the light component have been removed.

2 Claims, 14 Drawing Sheets

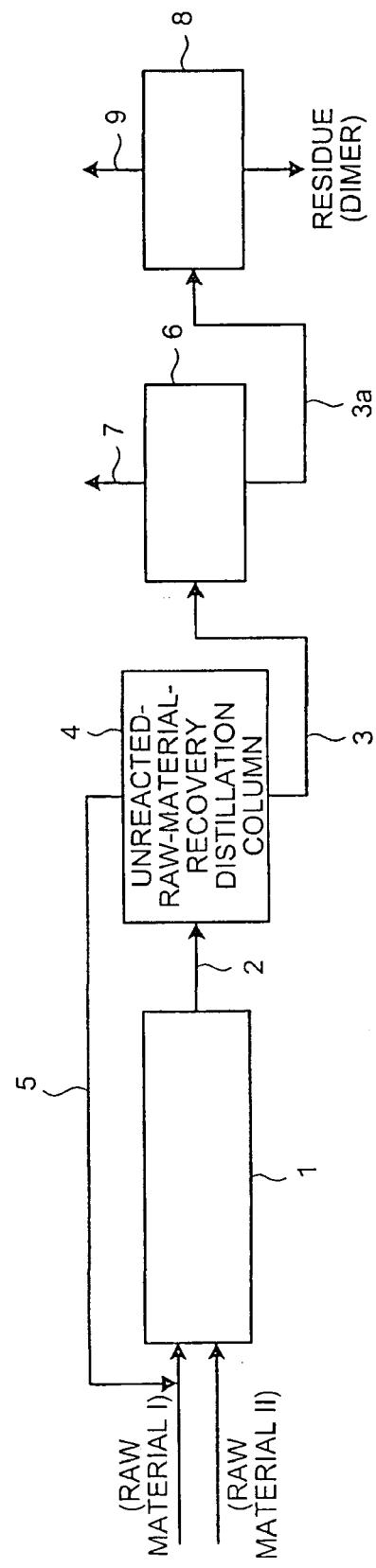

METHOD AND APPARATUS FOR PRODUCING MONO-LOWER-ALKYLMONO-ALKANOLAMINE

TECHNICAL FIELD

The present invention relates to a method and an apparatus for producing a mono-lower-alkylmonoalkanolamine that has high demand commercially by a reaction of a mono-lower-alkylamine and an alkylene oxide.

BACKGROUND ART

A mono-lower-alkylmonoalkanolamine is a useful compound which has a high commercial demand as an intermediate material for general organic synthesis, for example, a cationic flocculating agent, a drug or agricultural chemical intermediate, an etching liquid for resin, a softener for synthetic fibers, a corrosion inhibitor, a neutralizing agent for petroleum refining or petroleum process, or a dispersant.

The production of a mono-lower-alkylmonoalkanolamine by a reaction of a mono-lower-alkylamine and an alkylene oxide has so far been reported in literatures and others (for example, Nonpatent Literature 1).

In the reaction of a mono-lower-alkylamine and an alkylene oxide, both a mono-lower-alkylmonoalkanolamine and a mono-lower-alkyldialkanolamine are formed concurrently. In this reaction, for selectively obtaining a mono-lower-alkylmonoalkanolamine, the mono-lower-alkylamine must be used in large excess with respect to the amount of the alkylene oxide. For this reason, a great amount of unreacted mono-lower-alkylamine remains in the reaction.

As a method for producing a mono-lower-alkylmonoalkanolamine by a reaction of a mono-lower-alkylamine and an alkylene oxide, a zeolite catalyst method using zeolite as a catalyst has been proposed (Patent Document 1).

An example of a conventional apparatus for producing a mono-lower-alkylmonoalkanolamine using a zeolite catalyst is illustrated in FIG. 17. In FIG. 17, reference numeral 1 denotes a reactor, which is filled with a zeolite catalyst, and raw material I (mono-lower-alkylamine) and raw material II (alkylene oxide) are fed to the reactor 1 where they are reacted with each other by a zeolite catalyst method to produce a product 2 including unreacted raw materials. The product 2 including unreacted raw materials includes an unreacted mono-lower-alkylamine (unreacted raw material I) and an unreacted alkylene oxide (unreacted raw material II) as unreacted raw materials, and these unreacted raw materials and a reactive product 3 are separated by distillation by means of an unreacted-raw-material-recovery distillation column 4, and the unreacted mono-lower-alkylamine (raw material I) and alkylene oxide (raw material II) which are separated and recovered are fed back to the reactor 1 as an unreacted raw material 5.

Water and light component 7 are removed by a distillation method by means of a non-aqueous distillation column 6 from the reactive product 3 derived from the unreacted-raw-material-recovery distillation column 4, and a reactive product 3a from which the water and light component have been removed is fed to a purification and distillation column 8. The term "non-aqueous" means a state of the contents having a moisture content of 1000 ppm or less.

The reactive product 3a from which the water and light component have been removed is fed to the purification and distillation column 8 where a mono-lower-alkylmonoalkanolamine and a mono-lower-alkyldialkanolamine (dimer as a residue) formed by a reaction are separated by a distillation method, and the mono-lower-alkylmonoalkanolamine is recovered as a desired purified reactive product 9.

On the other hand, as a method for producing a mono-lower-alkylmonoalkanolamine using no zeolite catalyst, a method in which the production is conducted under, for example, supercritical conditions (conditions such that the temperature is 100 to 200° C. and the pressure is 17 to 24 megapascals [MPa]) has been proposed (Patent Document 2).

As a method for producing a mono-lower-alkylmonoalkanolamine by a reaction of a mono-lower-alkylamine and an alkylene oxide, a method in which the reaction is conducted in the presence of water (hereinafter, "water catalyst method") has been well known. However, this method has a problem in that the removal of a great amount of water by distillation in the purification system requires a large heat load.

Further, a method for producing monomethylaminoethanol from monomethylamine and ethylene oxide is disclosed (Patent Document 3). In the method described in Patent Document 3, crude liquid and alcohol are mixed and then fed to a distillation column for amine recovery system, or crude liquid and alcohol are individually fed through separate lines to the distillation column to recover unreacted monomethylamine.

Nonpatent Literature 1: "Surface Active Agent" by Ryohei ODA and Kazuhiro TERAMURA, p. 262-263, Maki Shoten, 1965
Patent Document 1: Japanese Patent Application Laid-open No. 2004-275933
Patent Document 2: Japanese Patent Application Laid-open No. S59-13751
Patent Document 3: Japanese Patent Application Laid-open No. H8-333310

DISCLOSURE OF INVENTION

Problem to be Solved by the Invention

However, the "zeolite catalyst method" described in Patent Document 1 has a problem in that deterioration of the catalyst causes lowering of the reaction rate or selectivity. In addition, there is a problem in that it is difficult to keep the temperature in the reactor 1 uniform and hence a product cannot be stably produced. Furthermore, the zeolite catalyst method has a problem in that a cooling device, such as a condenser, must be used in the distillation column that separates a mono-lower-alkylamine in the distillation step, increasing the energy consumption. The reason for this is as follows. In the zeolite catalyst method, solid (zeolite catalyst) and liquid (raw materials) are in contact to cause a reaction, and a reaction does not proceed at a site in which the solid and liquid are not in contact, so that the reaction in this method is of a heterogeneous system.

In the "supercritical method" described in Patent Document 2, there must be employed conditions such that the temperature is 100 to 200° C. and the pressure is 17 to 24 megapascals, and a problem arises in that increased power and cost are required in the operation.

In the technique described in Patent Document 3, for recovering monomethylamine, monomethylamine must be mixed with alcohol, and, for reusing the monomethylamine, a further distillation column is needed, causing problems in that the process is cumbersome and that the cost of facilities is increased.

Therefore, more efficient method and apparatus for producing a mono-lower-alkylmonoalkanolamine are desired.

Further, for improving the yield of mono-lower-alkyl-monoalkanolamine in production by the water catalyst method, the molar ratio of the alkylene oxide to the mono-lower-alkylamine must be reduced, and, in this case, the mono-lower-alkylamine is used while being circulated, causing a problem in that the reboiler load in the distillation column is larger to increase the energy consumption.

In view of the above problems, an object of the present invention is to provide a method and an apparatus for producing a mono-lower-alkylmonoalkanolamine, which are advantageous not only in that they are free from a problem of, for example, deterioration of the catalyst, which causes a problem when using a zeolite catalyst, but also in that the process fluid does not need to be supercritical fluid and a mono-lower-alkylmonoalkanolamine can be produced while saving energy.

Means for Solving Problem

To solve the problems as described above, according to a first aspect of the present invention, in a method for producing a mono-lower-alkylmonoalkanolamine by a reaction of a mono-lower-alkylamine and an alkylene oxide, reaction temperature is in a range of from 50 to 250° C., reaction pressure is in a range of from 0.1 to 10 megapascals, and water content is in a range of from 1 to 40 wt %.

According to a second aspect of the present invention, in the first aspect, in the method for producing a mono-lower-alkylmonoalkanolamine, ratio of an alkylene oxide raw material to a mono-lower-alkylamine raw material (alkylene oxide raw material/mono-lower-alkylamine raw material) is in a range of from 0.05 to 0.35.

According to a third aspect of the present invention, a method for producing a mono-lower-alkylmonoalkanolamine by a reaction of a mono-lower-alkylamine and an alkylene oxide includes introducing a product obtained in a reactor by synthesis into the reactor for heat exchange by indirect contact and self heat recovery of heat generated due to the reaction.

According to a fourth aspect of the present invention, in the third aspect, in the method for producing a mono-lower-alkylmonoalkanolamine, the reactor includes a plurality of stages for self heat recovery of the heat generated due to the reaction.

According to a fifth aspect of the present invention, in the third aspect, in the method for producing a mono-lower-alkylmonoalkanolamine, a product obtained is reduced in pressure into gas-liquid two phases before being introduced to the reactor.

According to a sixth aspect of the present invention, in the third aspect, in the method for producing a mono-lower-alkylmonoalkanolamine, the reactor is one of a shell and tube type reactor and a plate fin type reactor.

According to a seventh aspect of the present invention, in the third aspect, in the method for producing a mono-lower-alkylmonoalkanolamine, reaction temperature is in a range of from 50 to 250° C., reaction pressure is in a range of from 0.1 to 10 megapascals, and water content of raw materials fed to the reactor is in a range of from 1 to 40 wt %.

According to an eighth aspect of the present invention, in the third aspect, in the method for producing a mono-lower-alkylmonoalkanolamine, ratio of an alkylene oxide raw material to a mono-lower-alkylamine raw material (alkylene oxide raw material/mono-lower-alkylamine raw material) is in a range of from 0.05 to 0.35.

According to a ninth aspect of the present invention, in the third aspect, in the method for producing a mono-lower-alkylmonoalkanolamine, the product obtained is temporarily stored before being introduced to the reactor for heat exchange.

According to a tenth aspect of the present invention, in the third aspect, in the method for producing a mono-lower-alkylmonoalkanolamine, a heat-exchanged product is distilled, and moisture generated during the distillation and unreacted raw materials are fed back to a synthesis raw material side.

According to an eleventh aspect of the present invention, an apparatus for producing a mono-lower-alkylmonoalkanolamine by a reaction of a mono-lower-alkylamine and an alkylene oxide includes a reactor having a heat exchanger that feeds a reactive product to a heat exchange-type reactor body to indirectly self-heat-recover heat of reaction generated due to synthesis, an unreacted-raw-material distillation column that separates a product by distillation from a heat-recovered product that has been heat-exchanged to recover unreacted raw materials, and a purification and distillation column that purifies the product from which the unreacted raw materials have been removed and separates a desired reactive product by distillation.

According to a twelfth aspect of the present invention, in the eleventh aspect, in the apparatus for producing a mono-lower-alkylmonoalkanolamine, the reactor includes a plurality of stages for recovery of heat generated due to the reaction.

According to a thirteenth aspect of the present invention, in the eleventh aspect, in the apparatus for producing a mono-lower-alkylmonoalkanolamine, a reactive product obtained in the reactor is reduced in pressure into gas-liquid two phases, and then fed to the heat exchanger.

According to a fourteenth aspect of the present invention, in the eleventh aspect, in the apparatus for producing a mono-lower-alkylmonoalkanolamine, the reactor is one of a shell and tube type reactor and a plate fin type reactor.

According to a fifteenth aspect of the present invention, in the eleventh aspect, in the apparatus for producing a mono-lower-alkylmonoalkanolamine, reaction temperature is in a range of from 50 to 250° C., reaction pressure is in a range of from 0.1 to 10 megapascals, and water content of raw materials fed to the reactor is in a range of from 1 to 40 wt %.

According to a sixteenth aspect of the present invention, in the eleventh aspect, in the apparatus for producing a mono-lower-alkylmonoalkanolamine, ratio of an alkylene oxide raw material to a mono-lower-alkylamine raw material (alkylene oxide raw material/mono-lower-alkylamine raw material) is in a range of from 0.05 to 0.35.

According to a seventeenth aspect of the present invention, in the eleventh aspect, the apparatus for producing a mono-lower-alkylmonoalkanolamine further includes a storage tank in which the product obtained is temporarily stored before being introduced to the reactor for heat exchange.

Effect of the Invention

The present invention with the above configuration provides a method and an apparatus for producing a mono-lower-alkylmonoalkanolamine, which are advantageous in that a mono-lower-alkylmonoalkanolamine can be continuously produced in high yield.

BRIEF DESCRIPTION OF DRAWINGS

FIG. 17 is a schematic configuration diagram of a conventional apparatus for producing a mono-lower-alkylmonoalkanolamine.

EXPLANATIONS OF LETTERS OR NUMERALS

Figure 1:
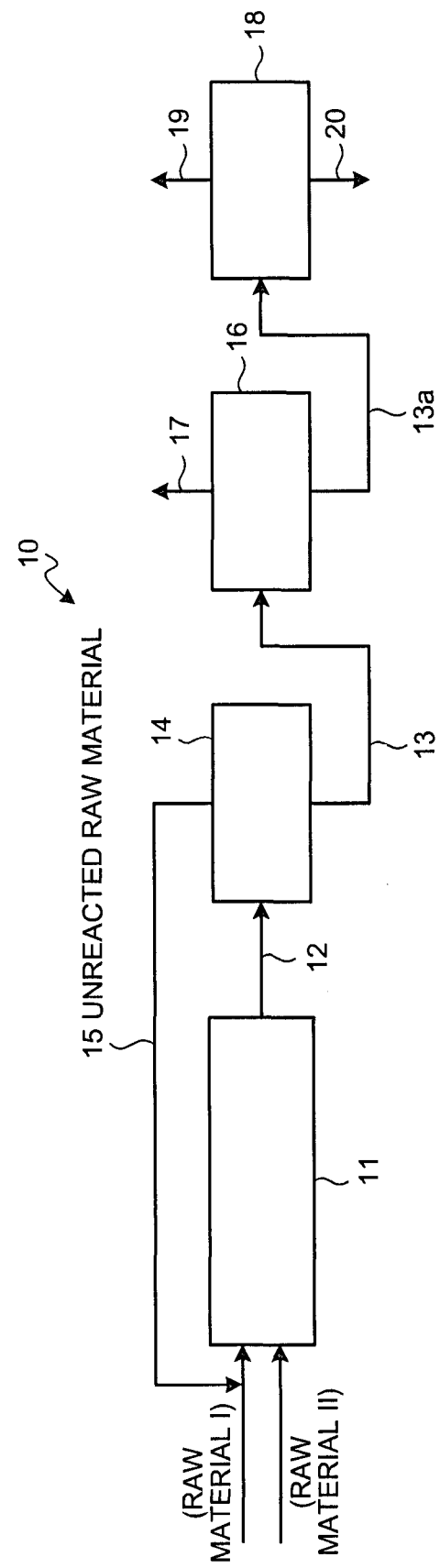
FIG. 1 is a schematic configuration diagram of an apparatus for producing a mono-lower-alkylmonoalkanolamine according to a first embodiment.

11 Reactor
11-1 to 11-4 First to fourth reactors
12 Reactive product including unreacted raw materials
13 Reactive product
14 Unreacted-raw-material-recovery distillation column
15 Unreacted raw material
16 Non-aqueous distillation column
17 Water and light component
18 Purification and distillation column
19 Desired reactive product (mono-lower-alkylmonoalkanolamine)
21 Residue (mono-lower-alkyldialkanolamine)
21 Flash drum
22 Unreacted-raw-material storage tank
V Reducing valve
A Heat exchanger

BEST MODE(S) FOR CARRYING OUT THE INVENTION

Embodiments of the present invention will be explained below in detail with reference to the accompanying drawings. The invention is not limited to the embodiments. In addition, constituent elements in the embodiments include those that can be easily assumed by those skilled in the art or that are substantially equivalent.

First Embodiment

An apparatus for producing a mono-lower-alkylmonoalkanolamine according to a first embodiment of the present invention is explained with reference to the accompanying drawings. FIG. 1 is a conceptual view of an apparatus for producing a mono-lower-alkylmonoalkanolamine according to the present embodiment (hereinafter, "amine producing apparatus"). As depicted in FIG. 1, a first amine producing apparatus 10 according to the present embodiment includes a reactor 11 that reacts a mono-lower-alkylamine (raw material I) and an alkylene oxide (raw material II) fed thereto, an unreacted-raw-material-recovery distillation column 14 that separates unreacted raw material 15 by distillation from a product 12 including unreacted raw materials obtained in the reactor 11, a non-aqueous distillation column 16 that removes water and light component 17 by a distillation method from a reactive product 13 from which the unreacted raw material 15 has been separated, and a purification and distillation column 18 that separates by distillation a desired reactive product (mono-lower-alkylmonoalkanolamine) 19 and residue (mono-lower-alkyldialkanolamine which is a dimer) 20 from a reactive product 13a from which the water and light component 17 have been removed.

With respect to the mono-lower-alkylamine as raw material I used in the present invention, there is no particular limitation, and a linear or branched chain monoalkylamine having 1 to 6 carbon atoms, such as monomethylamine, monoethylamine, mono-n-propylamine, mono isopropylamine, mono-n-butylamine, monoisobutylamine, mono-sec-butylamine, mono-t-butylamine, mono-n-pentylamine, isopentylamine, or mono-n-hexylamine, can be used. Preferably, monomethylamine, monoethylamine, mono-n-propylamine, monoisopropylamine, mono-n-butylamine, monoisobutylamine, or mono-t-butylamine can be used, and, especially preferably, monomethylamine, monoethylamine, mono-n-propylamine, monoisopropylamine, or mono-n-butylamine can be used.

With respect to the alkylene oxide as raw material II used in the present invention, there is no particular limitation, and preferably, an alkylene oxide having 2 to 4 carbon atoms, such as ethylene oxide, propylene oxide, or butylene oxide, can be used, and, especially preferably, ethylene oxide or propylene oxide can be used.

With respect to the conditions for the production of a mono-lower-alkylmonoalkanolamine in the present invention, it is preferred that the production is conducted at a reaction temperature in the reactor 11, for example, in the range of from 50 to 250° C. A preferred temperature is in the range of from 60 to 200° C., a more preferred temperature is in the range of from 60 to 150° C., and an especially preferred temperature is in the range of from 80 to 120° C.

It is preferred that the production is conducted at a pressure in the reactor 11, for example, in the range of from 0.1 to 10 megapascals. A preferred pressure is in the range of from 0.1 to 8 megapascals, and an especially preferred pressure is in the range of from 0.1 to 5 megapascals.

The present invention does not employ a reaction proceeding under supercritical conditions used in a conventional technique but a reaction proceeding under subcritical conditions, and therefore the reactor and its peripheral devices can have simple specifications with respect to pressure resistance.

Further, in the water catalyst method in the present invention, it is preferred that the method is conducted under conditions such that the water content of the raw materials fed to the reactor 11 is in the range of from 1 to 40 wt %. A preferred water content is in the range of from 5 to 30 wt %, and an especially preferred water content is in the range of from 5 to 20 wt %.

Figure 2:
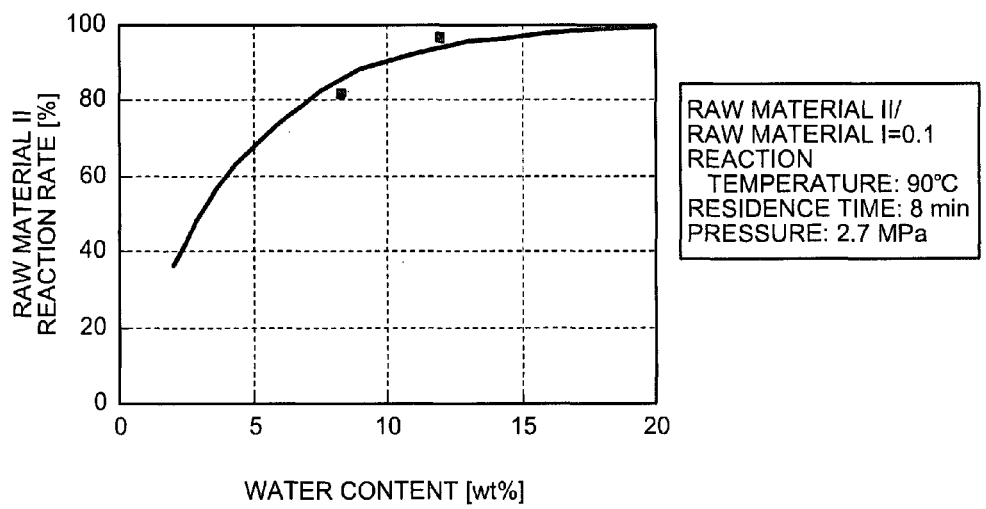
FIG. 2 is a graph of a relationship between a water content and a raw material II reaction rate.

With respect to the production of a mono-lower-alkylmonoalkanolamine by a water catalyst method in the present invention, it has been found that the reaction rate varies depending on the water content and, the higher the water content, the larger the reaction rate. For clearly showing this fact, a graph showing the relationship between a water content and a raw material II reaction rate is given in FIG. 2.

In the production of a mono-lower-alkylmonoalkanolamine by a water catalyst method, water is present, and hence an alkylene oxide as raw material II and water are reacted with each other to form a reaction intermediate. That is, this reaction has a reaction mechanism different from that of a reaction for forming a mono-lower-alkylmonoalkanolamine using a conventional zeolite catalyst in the zeolite catalyst method using a non-aqueous catalyst (see formulae (1) to (3)).

[Chemical Formula 1]

$$C_nH_{2n}O + H_2O \rightarrow C_nH_{2n+2}O_2 \quad (1)$$

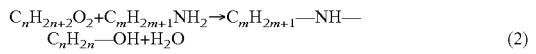

$$C_nH_{2n+2}O_2 + C_mH_{2m+1}NH_2 \rightarrow C_mH_{2m+1}-NH-C_nH_{2n}-OH + H_2O \quad (2)$$

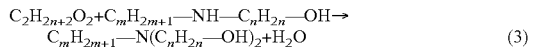

$$C_2H_{2n+2}O_2 + C_mH_{2m+1}-NH-C_nH_{2n}-OH \rightarrow C_mH_{2m+1}-N(C_nH_{2n}-OH)_2 + H_2O \quad (3)$$

As described above, the higher water content of the raw materials is advantageous. However, when the water content is too high, while the reaction time can be shortened, it is disadvantageous that the reboiler load in the purification system is considerably increased. Therefore, as illustrated in the Test examples below, from the relationship between a reaction time and a reboiler load, it is preferred that the water content of the raw materials fed to the reactor 11 is 5 to 20 wt %.

In the present invention, the ratio of raw materials fed is defined. That is, it is preferred that the molar ratio of the alkylene oxide raw material to the mono-lower-alkylamine raw material (alkylene oxide raw material II/mono-lower-alkylamine raw material I) is in the range of from 0.05 to 0.35.

When the molar ratio is more than 0.35, the reboiler load in the unreacted-raw-material-recovery distillation column (first distillation column) 14 that recovers unreacted raw materials is reduced, however, the reaction requires a prolonged time. On the other hand, when the molar ratio is less than 0.05, while the reaction time can be shortened, it is disadvantageous that the reboiler load is considerably increased.

Figure 3:
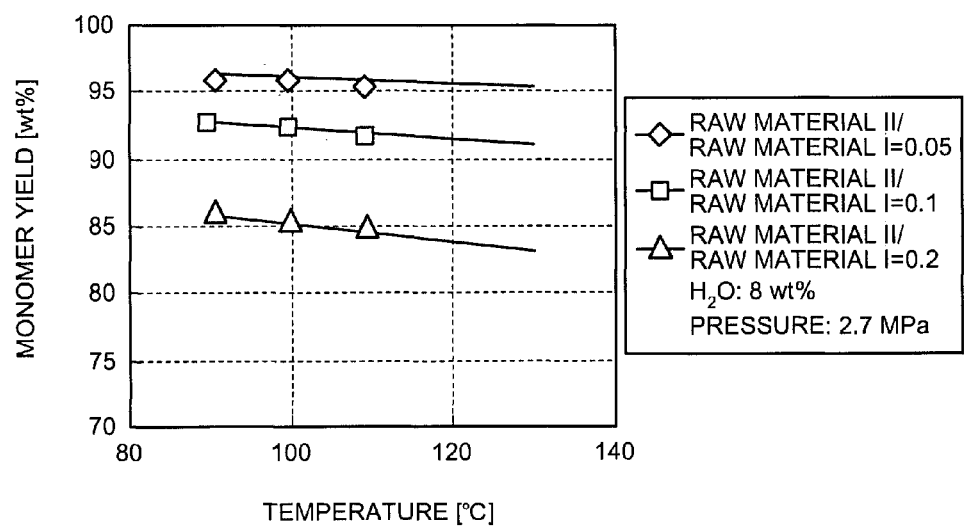
FIG. 3 is a graph of a relationship between a reaction temperature (° C.) and a yield (%) of monomer as a desired product.

The relationship between a reaction temperature (° C.) and a yield (%) of monomer as a desired product is illustrated in FIG. 3.

In the test of production of a mono-lower-alkylmonoalkanolamine by a water catalyst method in the present invention, when the water content is 8 wt % and the pressure in the reactor is 2.7 megapascals, the raw material II/raw material I molar ratio is changed to 0.05, 0.1, and 0.2 and the reaction temperature is changed to 90° C., 100° C., and 110° C., and the results are illustrated in FIG. 3.

As illustrated in FIG. 3, it has been found that the smaller the raw material molar ratio, the more excellent the reaction efficiency, and that the lower the reaction temperature, the more excellent the reaction efficiency.

From the above, it has been found that the smaller the molar ratio, or the lower the reaction temperature, the more excellent the production efficiency for a mono-lower-alkylmonoalkanolamine which is the desired reactive product 19.

Figure 4:
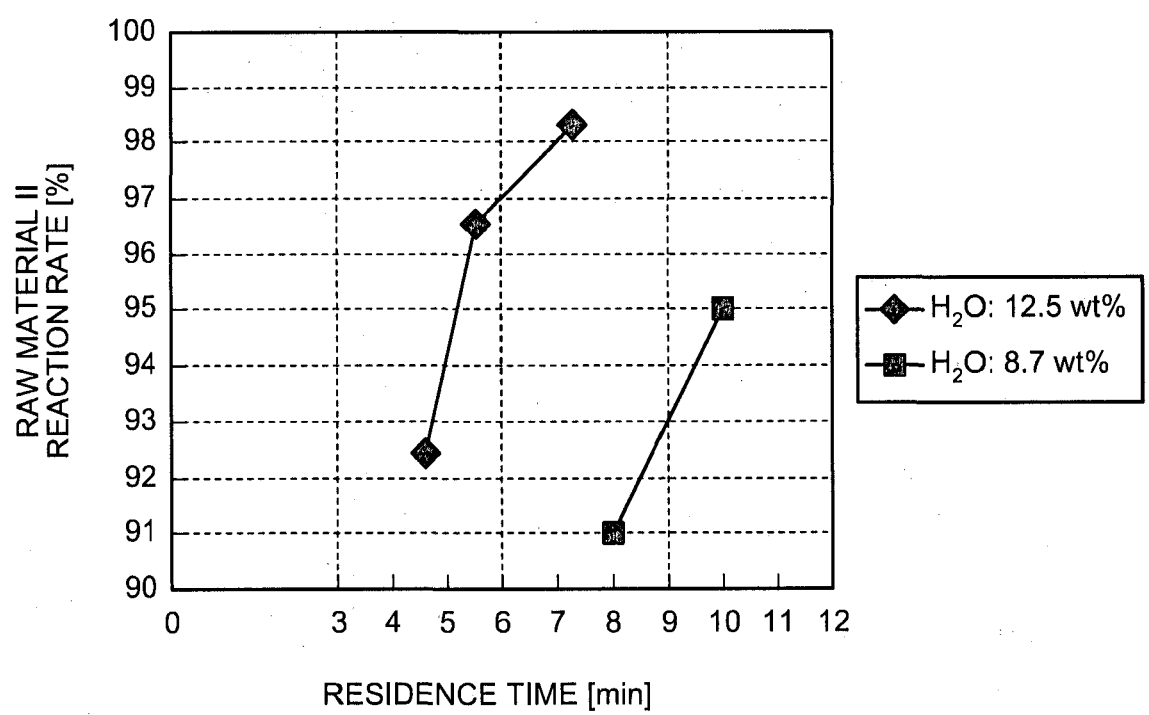
FIG. 4 is a graph of a relationship between a reaction residence time (minute) and a raw material II reaction rate (%).

The relationship between a reaction residence time (minute) and a raw material II reaction rate (%) is illustrated in FIG. 4.

In the test of production of a mono-lower-alkylmonoalkanolamine by a water catalyst method in the present invention, when the water content is 12.5 wt %, the reaction temperature is 90° C., the pressure in the reactor is 2.0 megapascals, and the raw material II/raw material I molar ratio is 0.1, the residence time is changed to 4.5 minutes, 5.5 minutes, and 7.5 minutes, and the results of measurement of the raw material II reaction rate (%) are illustrated in FIG. 4. In addition, when the water content is 8.7 wt %, the reaction temperature is 90° C., the pressure in the reactor is 2.0 megapascals, and the raw material II/raw material I molar ratio is 0.1, the residence time is changed to 8 minutes and 10 minutes, and the results of measurement of the raw material II reaction rate (%) are illustrated in FIG. 4.

As illustrated in FIG. 4, it has been found that, under the above conditions (water content is 12.5 wt % or 8.7 wt %), the longer the residence time, the larger the amount of raw material II consumed, or the more excellent the reaction efficiency. Further, it has been found that the higher the water content, the more excellent the reaction efficiency.

When (1) the temperature range (50 to 250° C.), (2) the pressure range (0.1 to 10 megapascals), (3) the water content (5 to 20 wt %), and the raw material molar ratio (0.05 to 0.35) are in the respective predetermined ranges defined in the present invention and the reaction system is under subcritical conditions, a mild reaction proceeds in a homogeneous liquid phase system in the reactor 11, so that a mono-lower-alkylmonoalkanolamine can be efficiently produced by a water catalyst method.

The reason for this is as follows. In a conventional zeolite method, solid (zeolite catalyst) and liquid (raw materials) are in contact to cause a reaction, and a reaction does not proceed at a site in which the solid and liquid are not in contact, so that the reaction in this method is of a heterogeneous system, and the efficiency of reaction varies depending on the size or packed state of the catalyst. By contrast, in the water catalyst method in the present invention, a reaction proceeds only in the liquid, and hence the reaction uniformly proceeds irrespective of the form of reaction site in the reactor, thus making it possible to efficiently produce a mono-lower-alkylmonoalkanolamine.

The present invention is free from a problem of deterioration of the catalyst, which is a problem when using a conventional zeolite catalyst, and can stably produce a mono-lower-alkylmonoalkanolamine as a desired product.

In the water catalyst method, unlike a conventional method, the reaction process fluid does not need to be supercritical fluid, and the configuration of the apparatus can be simplified, and further a mono-lower-alkylmonoalkanolamine as a desired product can be stably produced while saving energy.

Second Embodiment

Figure 5:
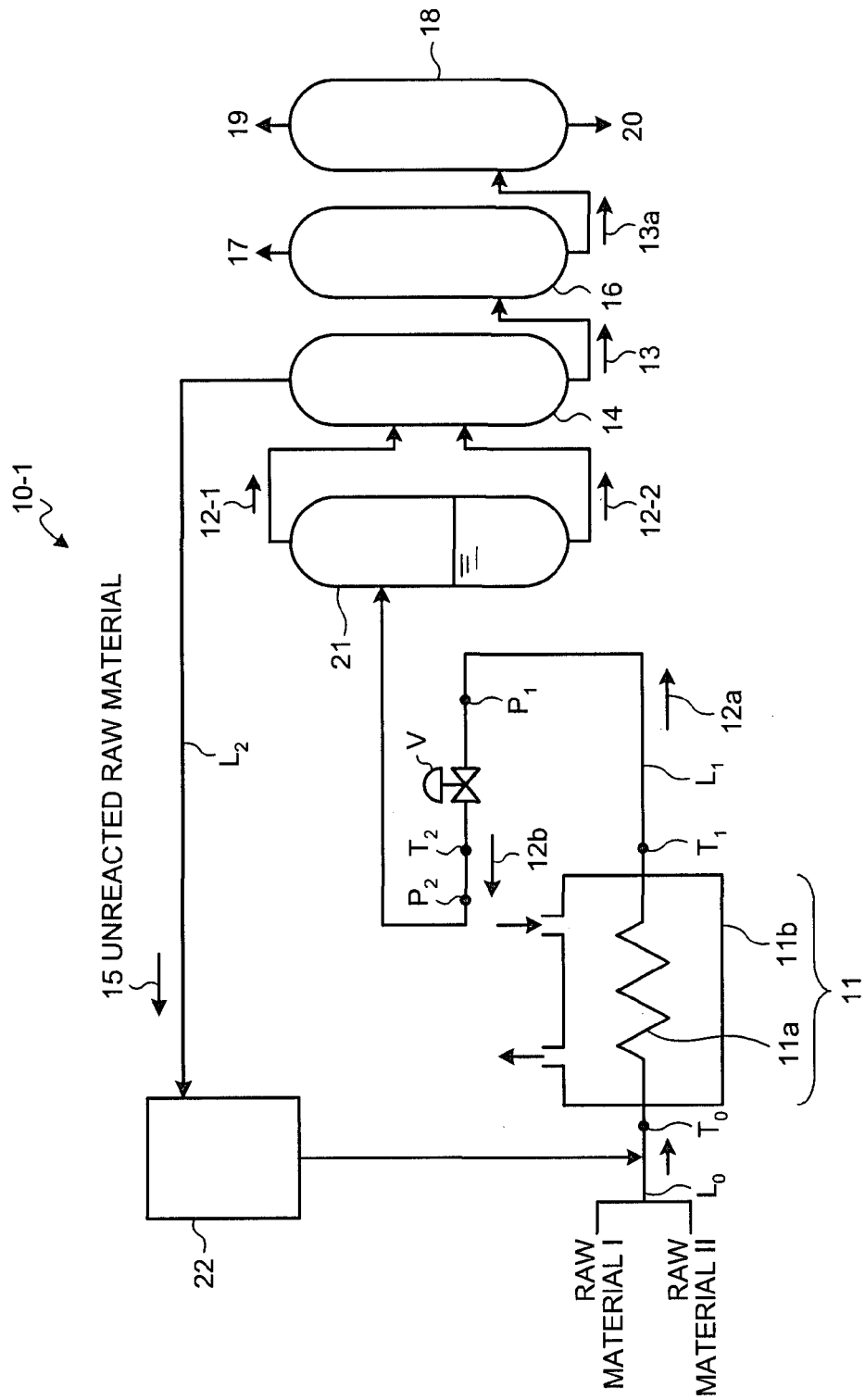
FIG. 5 is a schematic configuration diagram of an apparatus for producing a mono-lower-alkylmonoalkanolamine according to a second embodiment.

An apparatus for producing a mono-lower-alkylmonoalkanolamine according to a second embodiment of the present invention is described specifically with reference to the accompanying drawing. FIG. 5 is a conceptual view of an apparatus for producing a mono-lower-alkylmonoalkanolamine according to the present embodiment. As illustrated in FIG. 5, a first amine producing apparatus 10-1 according to the present embodiment includes a shell and tube type reactor (hereinafter "reactor") 11 that reacts a mono-lower-alkylamine (raw material I) and an alkylene oxide (raw material II) fed through a raw material feed line $L_0$, a reducing valve V formed in a product feed line $L_1$, for reducing the pressure for a product 12a including unreacted raw materials obtained in the reactor 11 to form a gas-liquid two phase product 12b, a flash drum 21 that flashes the gas-liquid two phase product 12b, the unreacted-raw-material-recovery distillation column 14 that separates by distillation an evaporated product 12-1 and a liquid product 12-2 obtained in the flash drum 21 into the unreacted raw material 15 and the reactive product 13 to recover the unreacted raw material 15, the non-aqueous distillation column 16 that removes the water and light component 17 by a distillation method from the reactive product 13 from which the unreacted raw material 15 has been separated, and the purification and distillation column 18 that purifies the reactive product 13a from which the water and light component 17 have been removed and separates it by distillation into the desired reactive product (mono-lower-alkylmonoalkanolamine) 19 and the residue (mono-lower-alkyldialkanolamine) 20.

In FIG. 5, reference numeral 22 denotes an unreacted-raw-material storage tank that temporarily stores the separated unreacted raw material 15. Therefore, the unreacted raw material 15 is fed through an unreacted raw material feed line $L_2$ and temporarily stored in the unreacted-raw-material storage tank 22, and, if necessary, fed from the unreacted-raw-material storage tank 22 back to the raw material feed line $L_0$ and reused in the reaction.

In the production in the present invention, with respect to the reactor, there is no particular limitation. When the shell and tube type reactor is used, heat can be supplied to the reactor from the outside to control the temperature in the reactor 11 to be uniform.

When the apparatus for producing a mono-lower-alkylmonoalkanolamine illustrated in FIG. 5 is used, the reaction conditions, i.e., (1) the temperature range (50 to 250° C.), (2) the pressure range (0.1 to 10 megapascals), (3) the water content (5 to 20 wt %), and the raw material molar ratio (0.05 to 0.35) are in the respective predetermined ranges, and the reaction system is under subcritical conditions, a mild reaction proceeds in a homogeneous liquid phase system in the reactor 11, so that a mono-lower-alkylmonoalkanolamine can be efficiently produced by a water catalyst method.

Third Embodiment

Figure 6:
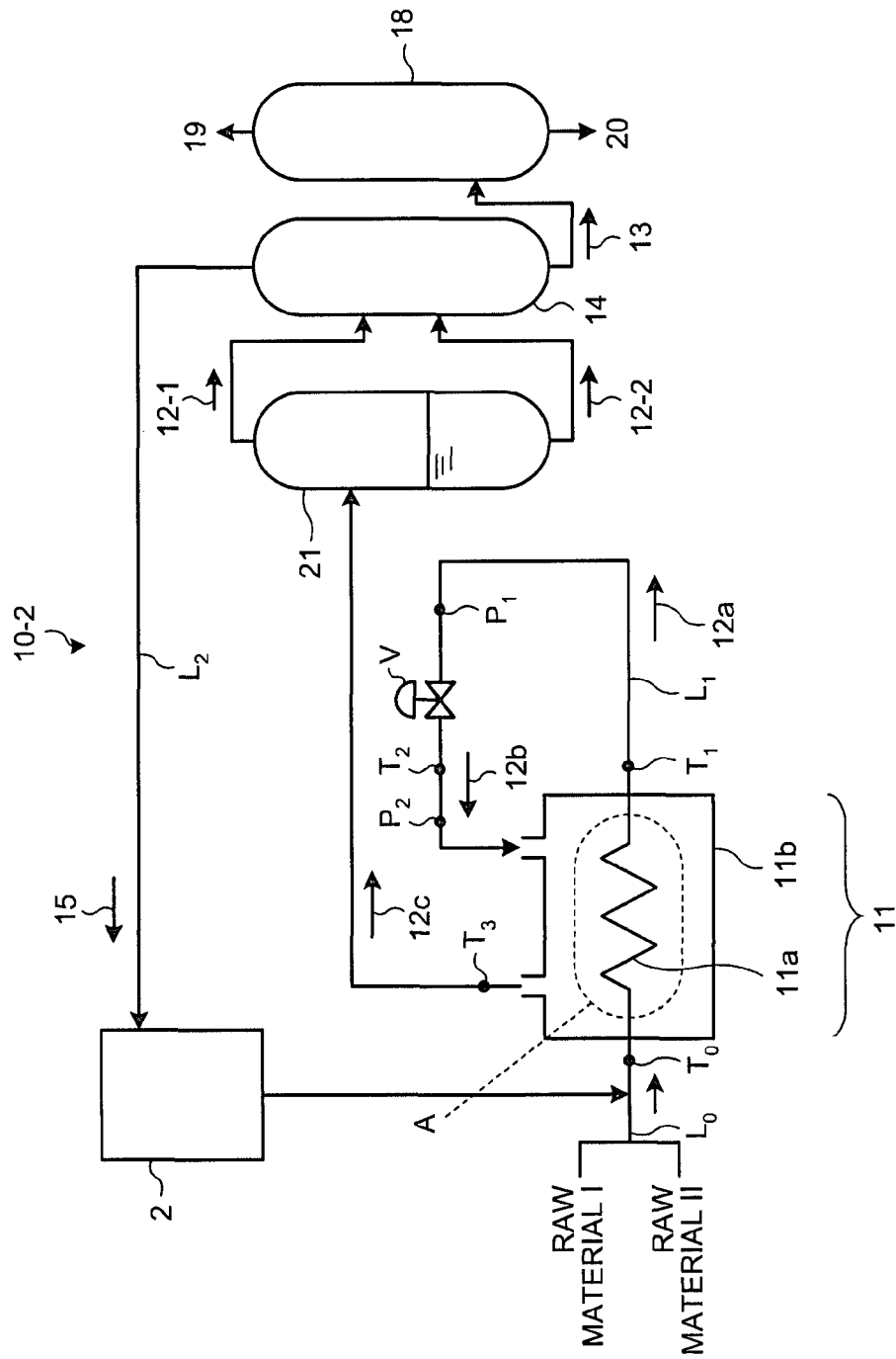
FIG. 6 is a schematic configuration diagram of an apparatus for producing a mono-lower-alkylmonoalkanolamine according to a third embodiment.

An apparatus for producing a mono-lower-alkylmonoalkanolamine according to a third embodiment of the present invention is described with reference to the accompanying drawings. FIG. 6 is a conceptual view of an apparatus for producing a mono-lower-alkylmonoalkanolamine according to the present embodiment (hereinafter "amine producing apparatus"). As illustrated in FIG. 6, a second amine producing apparatus 10-2 according to the present embodiment includes a shell and tube type reactor (hereinafter "reactor") 11 that reacts a mono-lower-alkylamine (raw material I) and an alkylene oxide (raw material II) fed through the raw material feed line $L_0$, the reducing valve V formed in the reactive product feed line $L_1$, for reducing the pressure for the product 12a including unreacted raw materials obtained in the reactor to form the gas-liquid two phase product 12b, a heat exchanger A that feeds the gas-liquid two phase product 12b reduced in pressure to a shell 11b of the reactor 11 to indirectly self-heat-recover heat of reaction generated due to an exothermic reaction of the raw materials in a tube 11a, the flash drum 21 that flashes a heat-recovered product 12c which has been heat-exchanged, the unreacted-raw-material-recovery distillation column 14 that separates the evaporated product 12-1 and the liquid product 12-2 obtained in the flash drum 21 by distillation from the included unreacted raw material 15 and the product 13 to recover the unreacted raw material 15, and the purification and distillation column 18 that purifies the product 13 from which the unreacted raw material 15 has been separated and separates it by distillation into the desired reactive product (mono-lower-alkylmonoalkanolamine) 19 and the residue (mono-lower-alkyldialkanolamine) 20.

In the present embodiment, the desired reactive product 19 can contain moisture, and the non-aqueous distillation column 16 illustrated in FIG. 5 that removes the water and light component 17 by a distillation method is not provided. However, when the moisture content is lowered to a predetermined value or less, the non-aqueous distillation column can be provided as necessary.

In FIG. 6, reference symbol $T_0$ denotes temperature of the raw materials (mixture of raw material I and raw material II) fed to the reactor 11, $T_1$ denotes temperature of the product 12a including unreacted raw materials fed from the reactor 11, $T_2$ denotes temperature of the gas-liquid two phase product 12b reduced in pressure by the reducing valve V, and $T_3$ denotes temperature of the heat-recovered product 12c which has been heat-recovered in the reactor 11. Further, $P_1$ and $P_2$ denote pressure gauges for respectively measuring pressures upstream and downstream of the reducing valve V formed in the reactive product feed line $L_1$.

While the reactor 11 is a shell and tube type reactor in the present embodiment, any reactor, for example, a plate fin type reactor can be used as long as it can indirectly self-heat-recover heat of reaction to the gas-liquid two phase product 12b.

The reaction system is under the above-mentioned pressure conditions (in the range of from 0.1 to 10 megapascals), and the reactive product 12a including unreacted raw materials led from the reactor 11 is reduced in pressure by the reducing valve V to form the gas-liquid two phase product 12b in a gas-liquid two phase state, improving the heat recovery efficiency so that temperature $T_2$ on the product side is lower than temperature $T_0$ on the raw material side by about 5 to 20° C.

Alternatively, the product 12a including unreacted raw materials can be heat-recovered in a separate line to lower the temperature ($T_0 > T_2$) without using the reducing valve V.

In each of the distillation columns (the unreacted-raw-material-recovery distillation column 14 and the purification and distillation column 18), the conditions are preferably controlled so that the highest temperature in each reboiler becomes 185° C. or lower.

In the present invention, removal of heat of reaction generated due to an exothermic reaction is made in the gas-liquid two phase product 12b which is reactor outlet fluid, making it possible to effectively utilize the heat of reaction.

The heat-recovered product 12c heat-recovered in the reactor 11 is subjected to gas-liquid separation in the flash drum 21, and the evaporated product 12-1 and the liquid product 12-2 are fed to the unreacted-raw-material-recovery distillation column 14 where the product 13 is separated by distillation, recovering the unreacted raw material 15.

The product 13 from which the unreacted raw material 15 has been removed is fed to the purification and distillation column 18 where a mono-lower-alkylmonoalkanolamine which is the desired reactive product 19 is purified, separating a mono-lower-alkyldialkanolamine which is the residue 20.

The reactive product led from the reactor 11 in this manner is separated in the subsequent distillation step into the unreacted raw material (raw material I and raw material II) 15, water, the desired reactive product 19, and the residue 20. Prior to the distillation step, the heat of reaction caused in the reaction step is self-recovered in reactor 11, so that the reboiler load in the unreacted-raw-material-recovery distillation column 14 upon separating the unreacted raw material 15 can be considerably reduced.

Further, the reactive product 12a is used as a medium for heat exchange, and therefore there is no need to use cooling water for a condenser, so that the energy consumption in the whole of the synthesis system can be considerably reduced.

With respect to the mono-lower-alkylamine used in the present invention, there is no particular limitation, and a linear or branched chain monoalkylamine having 1 to 6 carbon atoms, such as monomethylamine, monoethylamine, mono-n-propylamine, monoisopropylamine, mono-n-butylamine, monoisobutylamine, mono-sec-butylamine, mono-t-butylamine, mono-n-pentylamine, isopentylamine, or mono-n-hexylamine, can be used, and, preferably, monomethylamine, monoethylamine, mono-n-propylamine, monoisopropylamine, mono-n-butylamine, monoisobutylamine, or mono-t-butylamine can be used, and, especially preferably, monomethylamine, monoethylamine, mono-n-propylamine, monoisopropylamine, or mono-n-butylamine can be used.

With respect to the alkylene oxide used in the present invention, there is no particular limitation. Preferably, an alkylene oxide having 2 to 4 carbon atoms, such as ethylene oxide, propylene oxide, or butylene oxide, can be used, and, especially preferably, ethylene oxide or propylene oxide can be used.

The production of the mono-lower-alkylmonoalkanolamine can be conducted at a temperature, for example, in the range of from 50 to 250° C. The pressure for operation can be, for example, 0.1 to 10 megapascals. It is preferred that the molar ratio of the alkylene oxide raw material to the mono-lower-alkylamine raw material (alkylene oxide raw material II/mono-lower-alkylamine raw material I) is in the range of from 0.05 to 0.35.

Figure 15:
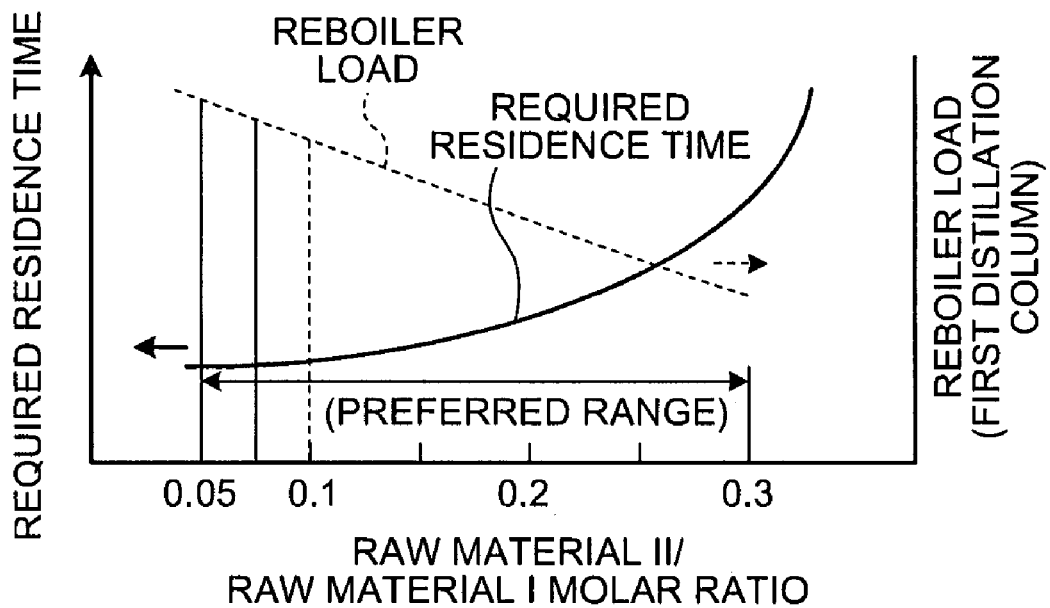
FIG. 15 is a graph of a relationship among a raw material II/raw material I molar ratio, a required residence time, and a reboiler load.

FIG. 15 is a graph of a relationship among a raw material II/raw material 1 molar ratio, a required residence time, and a reboiler load. As seen from FIG. 15, when the molar ratio is more than 0.35 (preferably 0.3), the reboiler load in the unreacted-raw-material-recovery distillation column (first distillation column) 14 for recovering unreacted raw materials is reduced, however, the reaction requires a prolonged time. On the other hand, when the molar ratio is less than 0.05, while the reaction time can be shortened, it is disadvantageous that the reboiler load is considerably increased.

When the concentration of raw material I in the unreacted raw materials fed back to the raw material feed line $L_0$ through the unreacted raw material feed line $L_2$ is high, the water content of the unreacted raw materials mixed with the fed raw material I (moisture content is 35%) is reduced, so that the reactivity becomes poor. On the other hand, when the recycled mono-lower-alkylamine (raw material I) concentration is low, the water content of the unreacted raw materials mixed with the raw material is increased, and therefore the reactivity is high, but the energy consumption in the unreacted-raw-material-recovery distillation column 14 is increased, and hence the column top concentration of the unreacted-raw-material-recovery distillation column 14 must be appropriately controlled.

Accordingly, in the present embodiment, an analyzer (not shown) for measuring a water content of the fluid (mainly of raw material I) withdrawn from the column top of the unreacted-raw-material-recovery distillation column 14 can be used in the apparatus so that the column top temperature is appropriately controlled, thus controlling the recycled mono-lower-alkylamine (raw material I) concentration.

Further, when a mixture of the recycled mono-lower-alkylamine and an aqueous solution of raw material I having a moisture content of 35% has a predetermined water content (for example, 10 wt %, 15 wt %, and 20 wt %), the reboiler load can be reduced as illustrated in the Test examples below.

By appropriately controlling the water content of the raw materials fed to the reactor 11 (for example, moisture content is 5 to 20 wt %), a mono-lower-alkylmonoalkanolamine can be produced economically.

Figure 16:
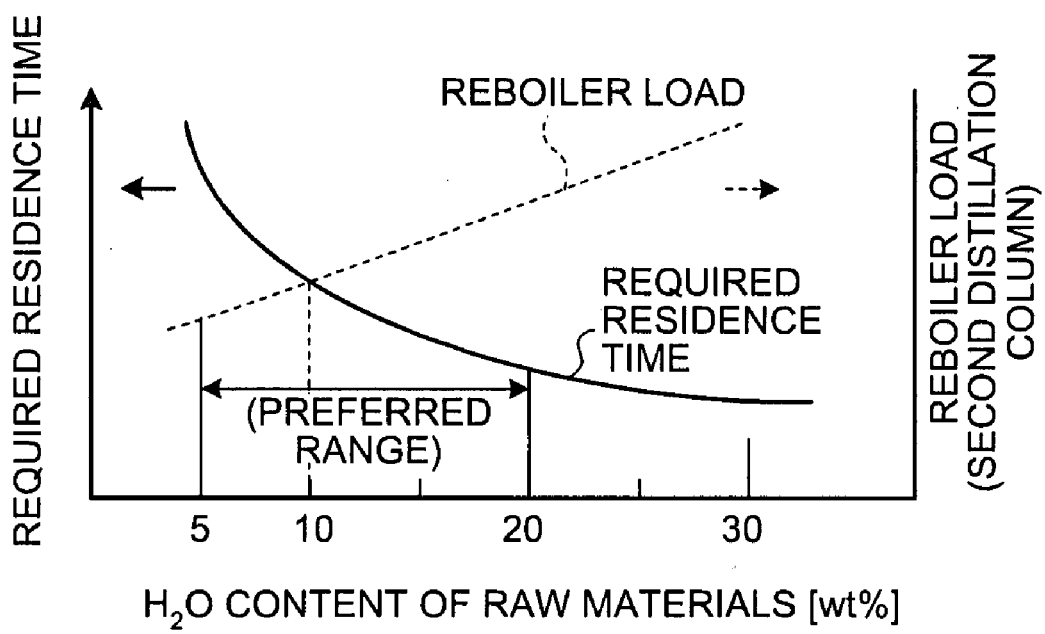
FIG. 16 is a graph of a relationship among a moisture content of a raw material, a required residence time, and a reboiler load.

As seen from FIG. 16, when the moisture content is less than 5 wt %, the reboiler load in the purification and distillation column (second distillation column) 18 for purifying the product is reduced, however, the reaction requires a prolonged time. On the other hand, when the moisture content is more than 20 wt %, while the reaction time can be shortened, it is disadvantageous that the reboiler load is considerably increased.

Fourth Embodiment

Figure 7:
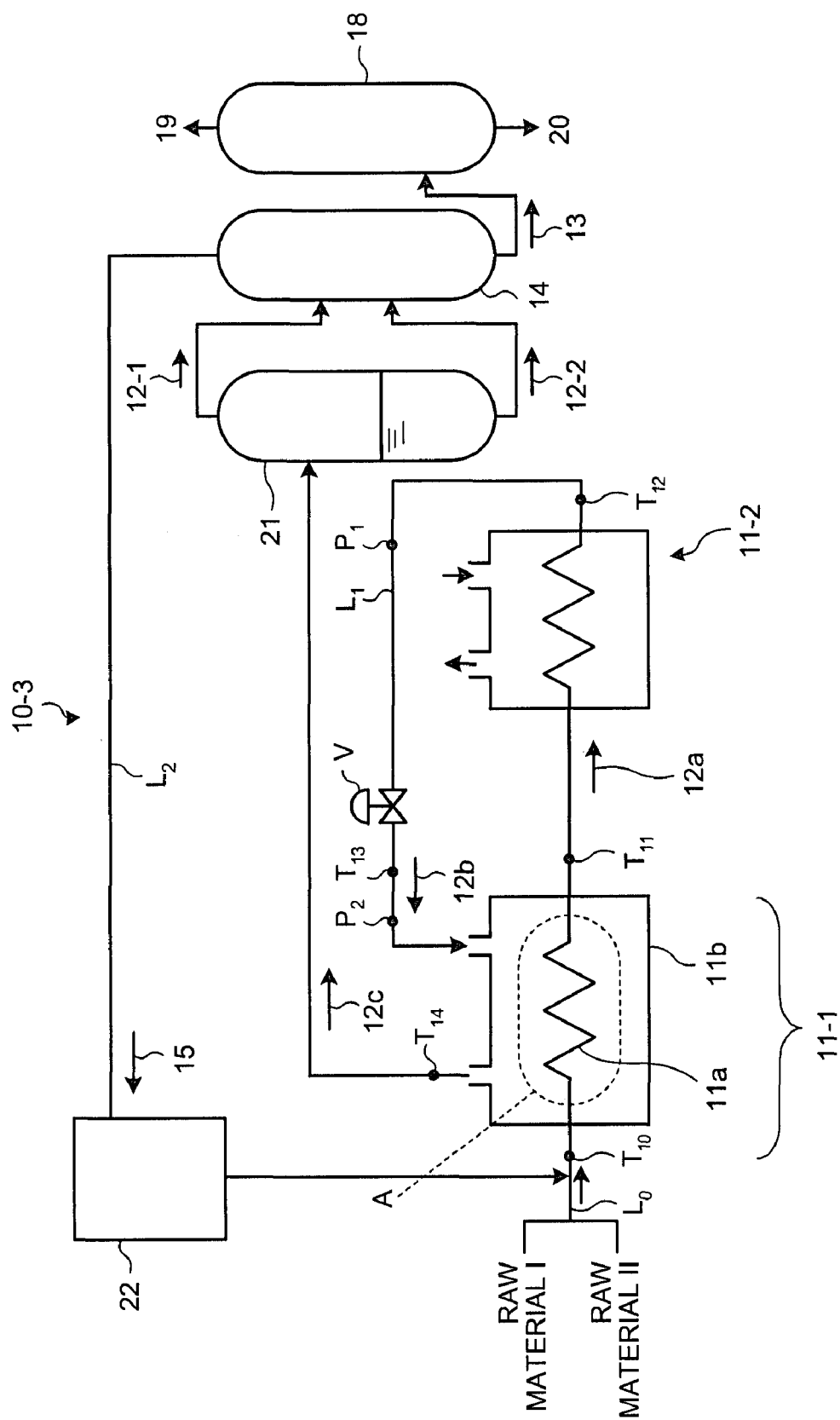
FIG. 7 is a schematic configuration diagram of an apparatus for producing a mono-lower-alkylmonoalkanolamine according to a fourth embodiment.

An apparatus for producing a mono-lower-alkylmonoalkanolamine according to a fourth embodiment of the present invention is described with reference to the accompanying drawing. FIG. 7 is a conceptual view of an amine producing apparatus according to the present embodiment. As illustrated in FIG. 7, a third amine producing apparatus 10-3 according to the present embodiment includes two stages of the reactors in the third embodiment arranged in series.

That is, as illustrated in FIG. 7, in the third amine producing apparatus 10-3, the product 12a including unreacted raw materials, which has been reacted in a first reactor 11-1, is led to a second reactor 11-2 where the reaction is completed, and then the reactive product 12a including unreacted raw materials is reduced in pressure by the reducing valve V formed in the reactive product feed line $L_1$ to form the gas-liquid two phase product 12b, and the gas-liquid two phase product 12b reduced in pressure is fed to the shell 11b of the first reactor 11-1, and heat of reaction generated due to an exothermic reaction of raw materials in the tube 11a is recovered in the heat exchanger A.

In FIG. 7, reference symbol $T_{10}$ denotes temperature of the raw materials (raw material II to raw material I) fed to the first reactor 11-1, $T_{11}$ denotes temperature of the product 12a including unreacted raw materials fed from the first reactor 11 first reactor 11-1, $T_{12}$ denotes temperature of the product 12a including unreacted raw materials fed from the second reactor 11-2, $T_{13}$ denotes temperature of the gas-liquid two phase product 12b reduced in pressure by the reducing valve V, and $T_{14}$ denotes temperature of the heat-recovered product 12c which has been heat-recovered in the reactor 11 first reactor 11-1.

In the present embodiment, the two stages of reactors (the first reactor 11-1 and the second reactor 11-2) are used, and therefore the reboiler load in the unreacted-raw-material-recovery distillation column 14 for separating unreacted raw materials can be reduced.

In the present embodiment, the two stages of reactors are used. However, it is not limited to two stages in the present invention, and a plurality of stages of reactors, for example, three or more stages of reactors can be used.

When three or more stages of reactors are used, it is more preferable that the product led from the final stage of reactor is fed to the shell of the first stage of reactor where heat generated due to the reaction is self-recovered.

Fifth Embodiment

Figure 8:
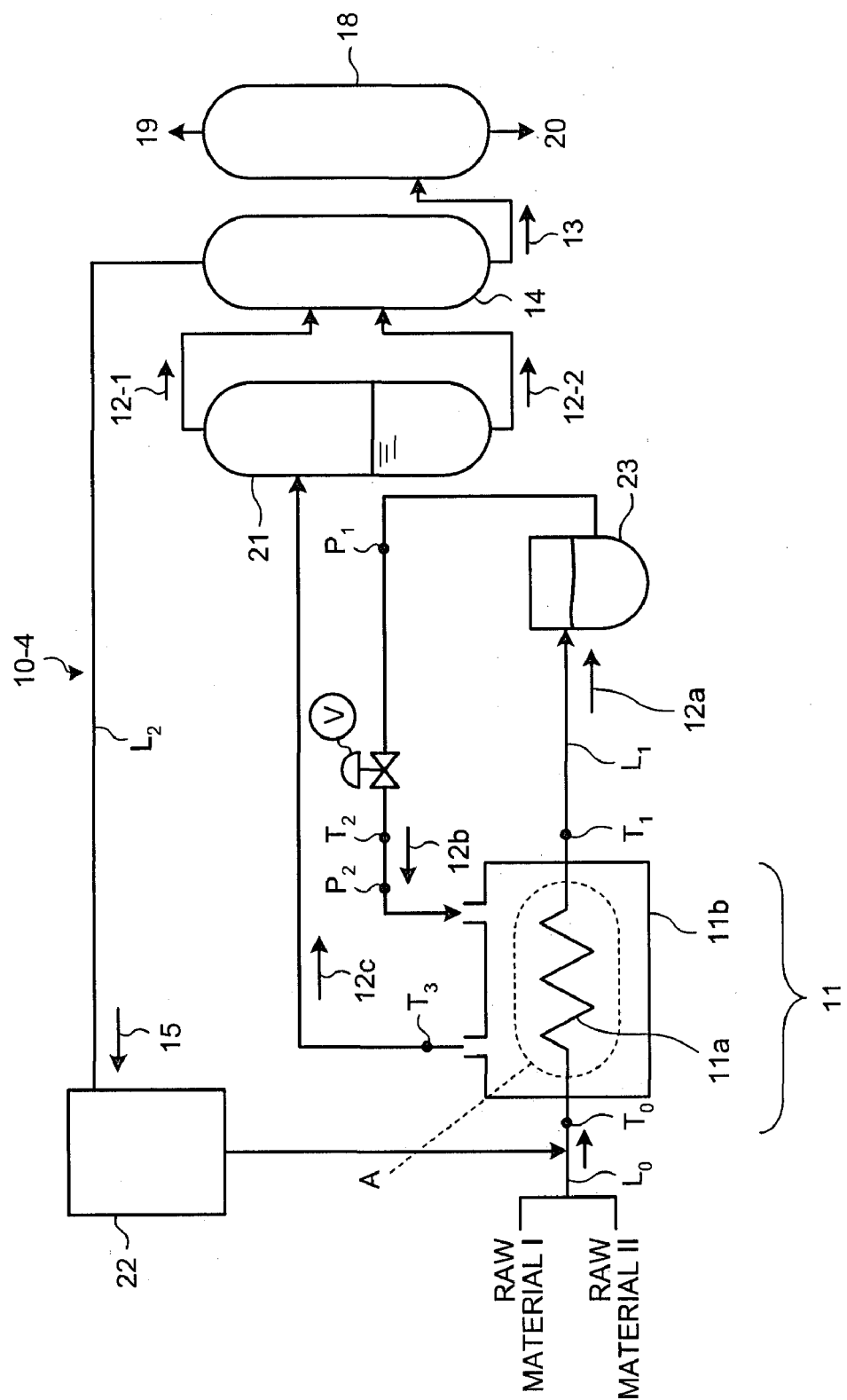
FIG. 8 is a schematic configuration diagram of an apparatus for producing a mono-lower-alkylmonoalkanolamine according to a fifth embodiment.

An apparatus for producing a mono-lower-alkylmonoalkanolamine according to a fifth embodiment of the present invention is described with reference to the accompanying drawings. FIG. 8 is a conceptual view of an amine producing apparatus according to the present embodiment. As illustrated in FIG. 8, in a fourth amine producing apparatus 10-4 according to the present embodiment, a reaction vessel 23 of a vessel type is provided downstream of the reactor 11 in the third embodiment so that the reaction is completed in the reaction vessel 23.

That is, the reaction is almost completed in the reactor 11 (for example, the raw material II reaction rate is 97% or more), and then the reaction is completed in the reaction vessel 23 so that the raw material II concentration becomes 100 ppm or less. In this case, a reaction residence time can be secured, thus improving the yield of a desired product.

In addition, the reaction temperature is kept to a predetermined low temperature to suppress the formation of the residue (mono-lower-alkyldialkanolamine) 20, making it possible to improve the yield of a desired product.

Figure 14:
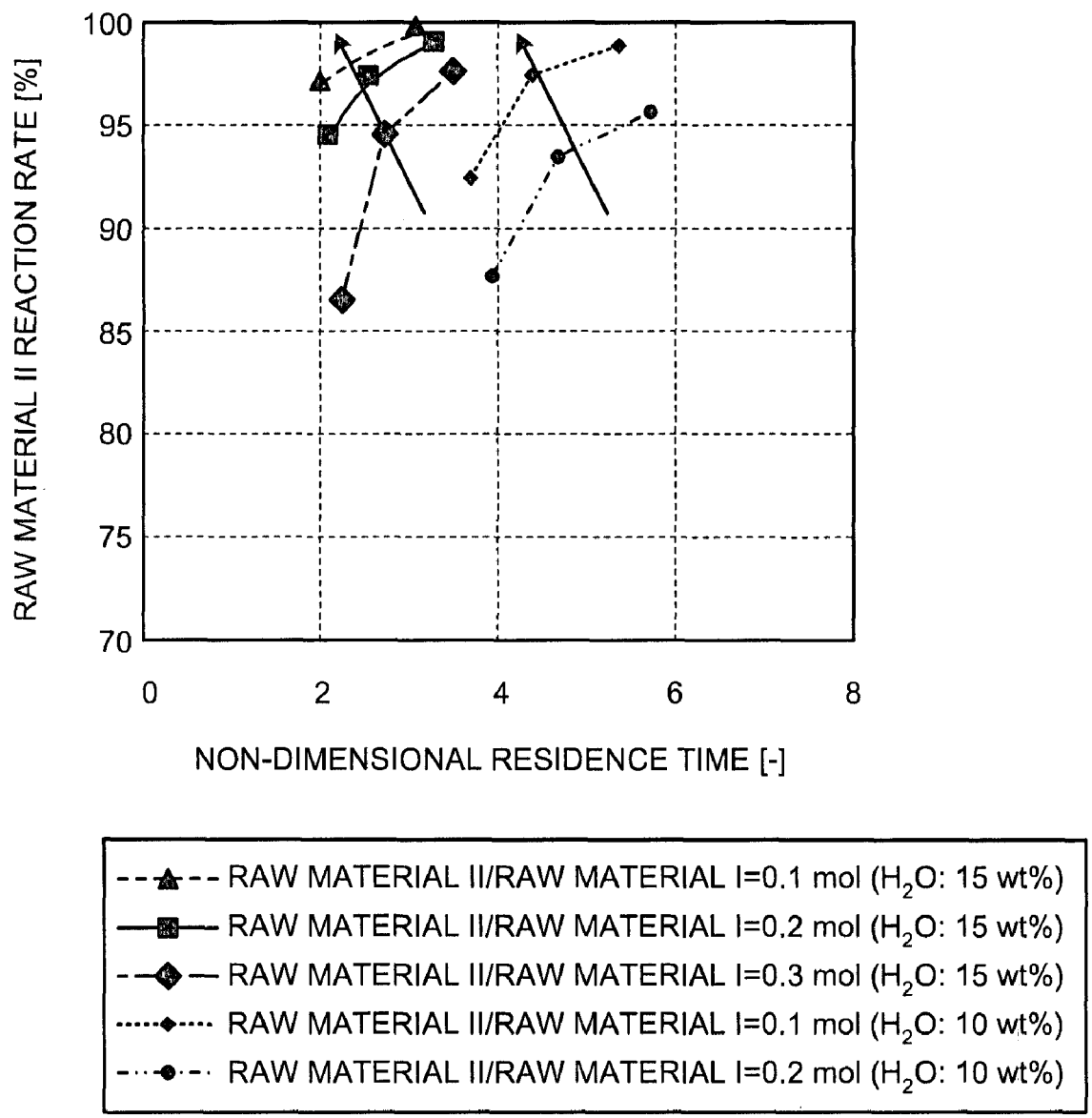
FIG. 14 is a graph of a relationship between a residence time and a reaction raw material II reaction rate.

That is, as seen from FIG. 14, when the reaction residence time is prolonged, the alkylene oxide raw material (raw material II) reaction rate is improved.

From the results illustrated in FIG. 14, it has been found that, when the ratio of the alkylene oxide raw material (raw material II) to the mono-lower-alkylamine raw material (raw material I) and the moisture content are increased (the moisture content is 15 wt % rather than 10 wt %), the raw material II reaction rate is improved.

Further, it has been found that, when the raw material II reaction rate is 95% or more, the reaction does not proceed and a prolonged residence time is required.

TEST EXAMPLES

The present invention will be explained below in more detail with reference to Test examples, which should not be construed as limiting the scope of the present invention.

Test Example 1

Figure 9:
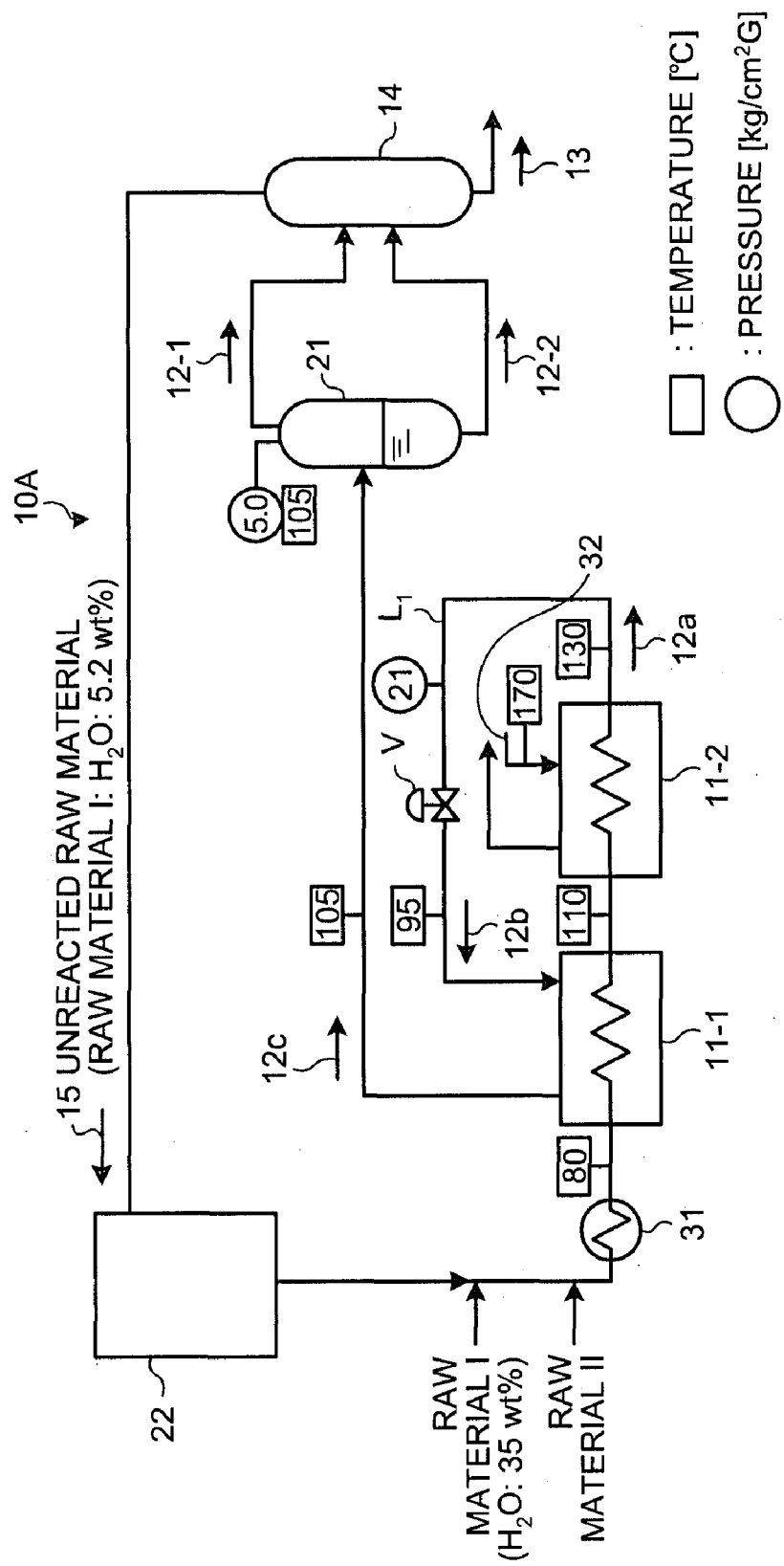
FIG. 9 is a schematic configuration diagram of an apparatus for producing a mono-lower-alkylmonoalkanolamine in Test example 1.

An amine producing apparatus 10A in Test example 1 having the same configuration as that in the fourth embodiment is illustrated in FIG. 9. The conditions for operation of the first reactor 11-1, the second reactor 11-2, the reducing valve V, the flash drum 21, and the unreacted-raw-material-recovery distillation column 14 are shown below. Reference numeral 31 denotes a heat exchanger, and 32 denotes a water vapor.

(The First Reactor 11-1)
Inlet temperature: 80° C.
Outlet temperature: 110° C.
(The Second Reactor 11-2)
Inlet temperature: 110° C.
Outlet temperature: 130° C.
(Reducing Pressure by the Reducing Valve V)
The product 12a including unreacted raw materials at 21 kg/cm$^2$G at 130° C. was reduced in pressure to 5.0 kg/cm$^2$G at 105° C. to form the gas-liquid two phase product 12b. Raw material II/raw material I molar ratio at the inlet of the first reactor: 0.1
Moisture content at the inlet of the first reactor: 8 wt % (The unreacted-raw-material-recovery distillation column 14)
Pressure (at the column top): 101.33 to 500 kPa
Temperature (Reboiler highest temperature): 185° C.
Fed raw material I (moisture content: 35 wt %), recycled unreacted raw material 15 (moisture content: 5.2 wt %)
The temperature distribution in the first reactor 11-1 being operated is depicted in FIG. 10.

Figure 10:
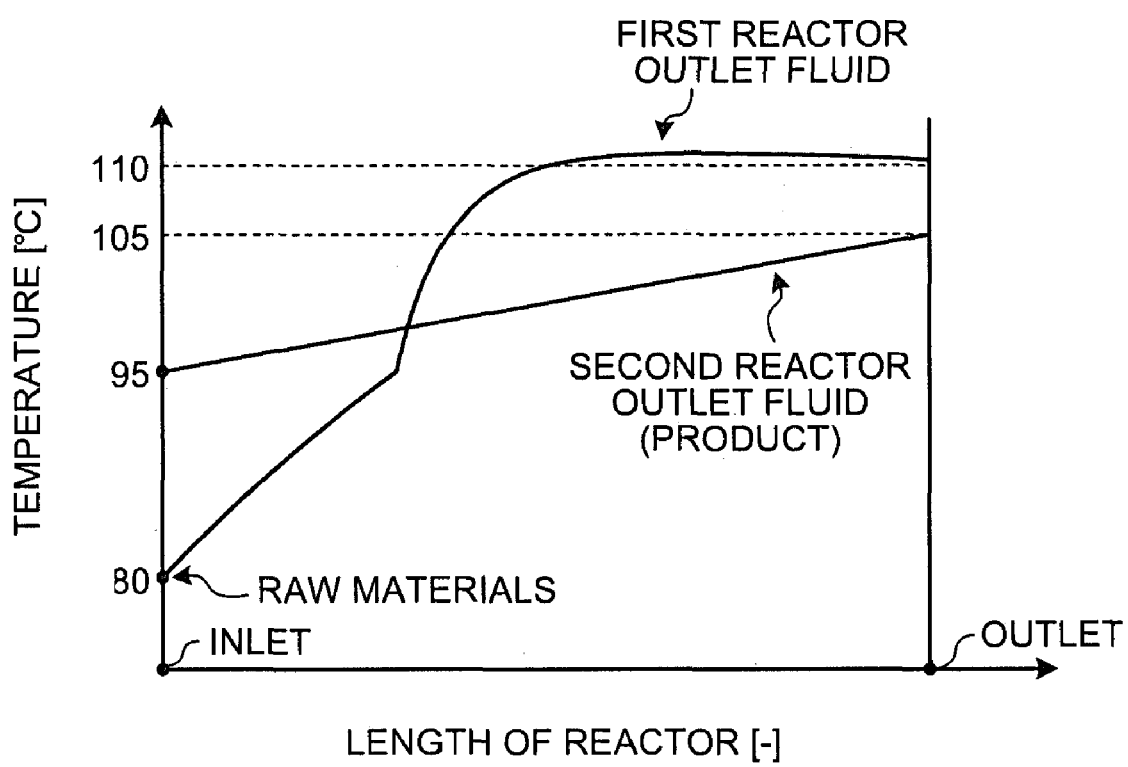
FIG. 10 is a graph of a temperature distribution of a first reactor in Test example 1.

In FIG. 10, the abscissa and ordinate give a length of the reactor and a temperature, respectively. At the inlet of the first reactor 11-1, the raw materials cause preheating. When the preheating increases the temperature to 95° C. or higher, a reaction is accelerated, so that marked temperature elevation is confirmed. The gas-liquid two phase product 12b reduced in pressure by the reducing valve V is led to the reaction site, so that the heat of reaction is self-recovered, achieving temperature elevation to 105° C.

Removal of the heat of reaction generated in the first reactor 11-1 is made by heat recovery using the obtained product without using conventional cooling water, enabling effective utilization of the heat of reaction.

Test Example 2

Figure 11:
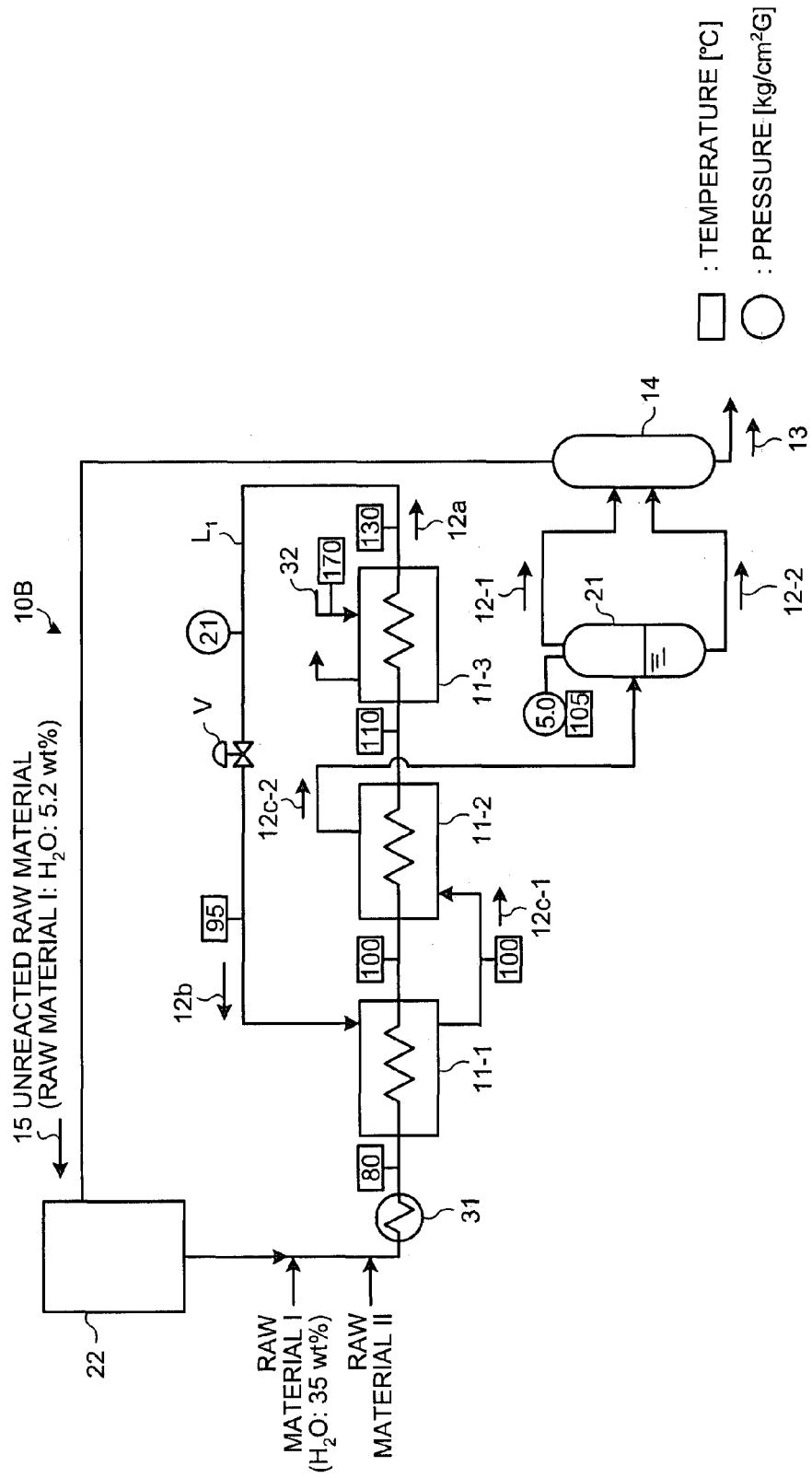
FIG. 11 a schematic configuration diagram of an apparatus for producing a mono-lower-alkylmonoalkanolamine in Test example 2.

An amine producing apparatus 10B in Test example 2 is illustrated in FIG. 11. As illustrated in FIG. 11, the amine producing apparatus 10B in the present Test Example has a third reactor 11-3 further provided in series in the amine producing apparatus 10A in Test example 1.

Figure 12:
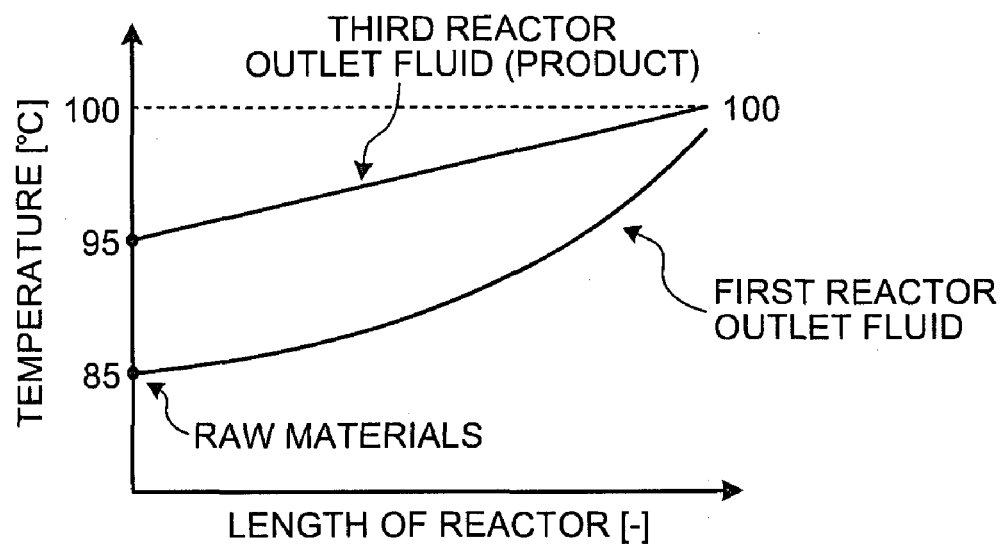
FIG. 12 is a graph of a temperature distribution of a first reactor in Test example 2.

The conditions for operation of the first reactor 11-1, the second reactor 11-2, the third reactor 11-3, the reducing valve V, the flash drum 21, and the unreacted-raw-material-recovery distillation column 14 are shown below.
(The First Reactor 11-1)
Inlet temperature: 80° C.
Outlet temperature: 100° C.
(The Second Reactor 11-2)
Inlet temperature: 100° C.
Outlet temperature: 110° C.
(The Third Reactor 11-3)
Inlet temperature: 110° C.
Outlet temperature: 130° C.
(The Reducing Valve V)
The product 12a including unreacted raw materials at 21 kg/cm$^2$G at 130° C. was reduced in pressure to 5.0 kg/cm$^2$G at 105° C. to form the gas-liquid two phase product 12b. Raw material II/raw material 1 molar ratio at the inlet of the first reactor: 0.1 Moisture content at the inlet of the first reactor: 8 wt %
(The unreacted-raw-material-recovery distillation column 14)
Pressure (at the column top): 101.33 to 500 kPa
Temperature (Reboiler highest temperature): 185° C.
Fed raw material I (moisture content: 35 wt %), recycled unreacted raw material 15 (moisture content: 5.2 wt %)
The temperature distribution in the first reactor 11-1 being operated is illustrated in FIG. 12.
In FIG. 12, the horizontal axis and vertical axis represent a length of the reactor and a temperature, respectively. At the inlet of the first reactor 11-1, the raw materials cause preheating. Preheating causes the temperature at the outlet to be 100°

C., and a vigorous reaction does not occur. Accordingly, the fluid (the gas-liquid two phase product 12b) reduced in pressure and discharged from the outlet of the third reactor 11-3 is led to the reactor, and recovery of the heat of reaction is slight, causing only temperature elevation to 100° C.

Figure 13:
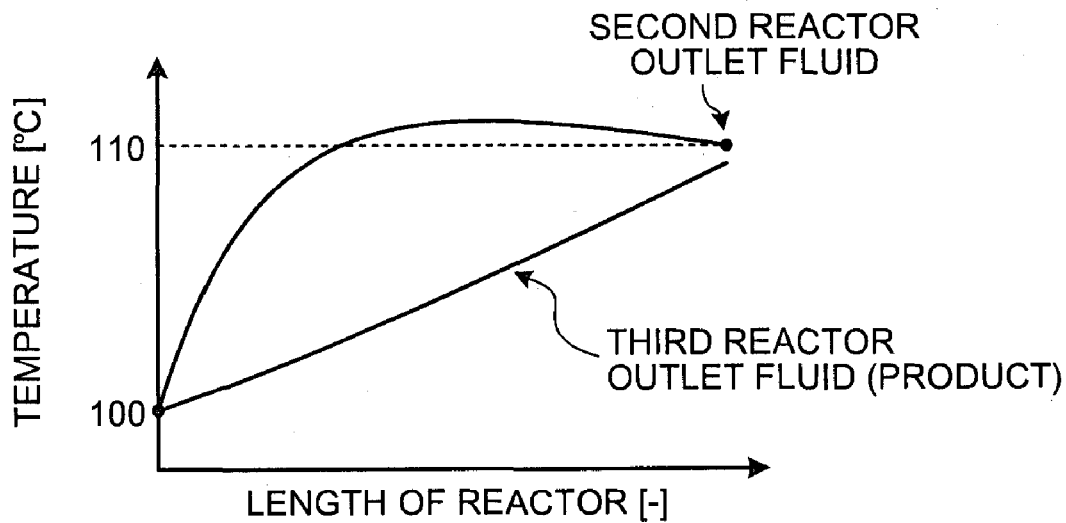
FIG. 13 is a graph of a temperature distribution of a second reactor in Test example 2.

FIG. 13 depicts a temperature distribution in the second reactor 11-2 being operated.

As depicted in FIG. 13, the temperature in the second reactor 11-2 is higher than 100° C., and a reaction is vigorously accelerated, so that marked temperature elevation is confirmed. A heat-recovered product 12c-1 heat-recovered in the first reactor 11-1 is led to the reaction site, so that the heat of reaction is recovered, discharging a heat-recovered product 12c-2 increased in temperature to 115° C. from the second reactor.

Removal of the heat of reaction generated in the first reactor 11-1 and the second reactor 11-2 is made by heat recovery using the obtained product without using conventional cooling water, enabling effective utilization of the heat of reaction.

INDUSTRIAL APPLICABILITY

As described above, according to the method and apparatus for producing a mono-lower-alkylmonoalkanolamine of the present invention, a mono-lower-alkylmonoalkanolamine can be effectively and continuously produced in high yield.

The invention claimed is:

1. A method for producing a mono-lower-alkylmonoalkanolamine by a reaction of a mono-lower-alkylamine and an alkylene oxide, the method comprising the steps of:
    feeding the mono-lower-alkylamine in excess with respect to the amount of the alkylene oxide in a reactor for selectively obtaining the mono-lower-alkylmonoalkanolamine;
    separating unreacted raw material by distillation from a product including unreacted raw materials obtained in the reactor, in an unreacted-raw-material-recovery distillation column downstream of the reactor; and
    returning the unreacted raw material separated from the unreacted-raw-material-recovery distillation column to the mono-lower-alkylamine raw material;
    wherein, in each step
    reaction temperature is in a range of from 50 to 250° C.,
    reaction pressure is in a range of from 0.1 to 10 megapascals, and
    water content is in a range of from 1 to 40 wt %.

2. The method for producing a mono-lower-alkylmonoalkanolamine according to claim 1, wherein ratio of an alkylene oxide raw material to a mono-lower-alkylamine raw material (alkylene oxide raw material/mono-lower-alkylamine raw material) is in a range of from 0.05 to 0.35.

* * * * *